(12) United States Patent
Kaufman et al.

(10) Patent No.: US 6,652,473 B2
(45) Date of Patent: *Nov. 25, 2003

(54) ULTRASONIC AND GROWTH FACTOR BONE-THERAPY: APPARATUS AND METHOD

(75) Inventors: Jonathan J. Kaufman, 112 Willow St., Suite 1A, Brooklyn, NY (US) 11201; Alessandro Chiabrera, Genoa (IT)

(73) Assignee: Jonathan J. Kaufman, Brooklyn, NY (US)

(*) Notice: Subject to any disclaimer, the term of this patent is extended or adjusted under 35 U.S.C. 154(b) by 114 days.

This patent is subject to a terminal disclaimer.

(21) Appl. No.: 09/814,088

(22) Filed: Mar. 21, 2001

(65) Prior Publication Data

US 2001/0027278 A1 Oct. 4, 2001

Related U.S. Application Data

(63) Continuation of application No. 09/232,101, filed on Jan. 15, 1999, now Pat. No. 6,231,528.

(51) Int. Cl.$^7$ .......................... A61H 1/00; A61M 35/00
(52) U.S. Cl. .................... 601/1; 601/2; 601/15; 604/20; 604/290
(58) Field of Search ............... 601/2, 1, 15; 604/19–22, 604/890.1, 892.1, 289, 290; 600/439; 607/50, 51; 514/946, 947, 964, 965

(56) References Cited

U.S. PATENT DOCUMENTS

| | | |
|---|---|---|
| 3,828,769 A | 8/1974 | Mettler |
| 4,105,017 A | 8/1978 | Ryaby et al. |
| 4,315,503 A | 2/1982 | Ryaby et al. |
| 4,530,360 A | 7/1985 | Duarte |
| 4,877,864 A | 10/1989 | Wang et al. |
| 4,928,959 A | 5/1990 | Bassett et al. |
| 4,993,413 A | 2/1991 | McLeod et al. |
| 5,003,965 A | 4/1991 | Talish et al. |
| 5,103,806 A | 4/1992 | McLeod et al. |

(List continued on next page.)

OTHER PUBLICATIONS

Buckwalter et al., "Healing of bones, cartilages, tendons, and ligaments: a new era," (1996), Lancet, 348 (suppl II): 18.*

Michael Hadjiargyrou et al., "Enhancement of Fracture Healing by Low Intensity Ultrasound", *Clinical Orthopaedics and Related Research*, 1998, No. 355S, pp. S216–S229.

Thomas K. Kristiansen et al., "Accelerated Healing of Distal Radial Fratures with the Use of Specific, Low–Intensity Ultrasound", *The Journal of Bone and Joint Surgery*, 1997, vol. 79–A, No. 7, pp. 961–973.

(List continued on next page.)

*Primary Examiner*—Shawna J Shaw
(74) *Attorney, Agent, or Firm*—Rader, Fishman & Grauer PLLC

(57) ABSTRACT

Non-invasive therapeutic treatment of bone in vivo using ultrasound in conjunction with application of a biochemical compound or bone growth factor is performed by subjecting bone to an ultrasound signal supplied to an ultrasound transducer placed on the skin of a bony member, and involving a repetitive finite duration signal consisting of plural frequencies that are in the ultrasonic range to 20 MHz. Concurrent with application of the ultrasound is the utilization of a bone growth factor applied to the skin of a bony member before stimulation with ultrasound. Ultrasonic stimulation is operative to transport the bone growth factor to the bone and then to synergistically enhance the interaction of the bone growth factor with the bone, whereby to induce healing, growth and ingrowth responses. In another embodiment, a vibrational or mechanical input together with a biochemical compound enhances both bone fracture healing and treats osteoporosis.

92 Claims, 6 Drawing Sheets

U.S. PATENT DOCUMENTS

| | | | |
|---|---|---|---|
| 5,128,326 | A | 7/1992 | Balazs et al. |
| 5,186,162 | A | 2/1993 | Talish et al. |
| 5,191,880 | A | 3/1993 | McLeod et al. |
| 5,195,940 | A | 3/1993 | Baylink |
| 5,195,941 | A | 3/1993 | Erickson et al. |
| 5,211,160 | A | 5/1993 | Talish et al. |
| 5,309,898 | A | 5/1994 | Kaufman et al. |
| 5,318,561 | A | 6/1994 | McLeod et al. |
| 5,320,622 | A | 6/1994 | Faccioli et al. |
| 5,330,410 | A | 7/1994 | Baylink |
| 5,354,557 | A | 10/1994 | Oppermann et al. |
| 5,458,130 | A | 10/1995 | Kaufman et al. |
| 5,520,612 | A | 5/1996 | Winder et al. |
| 5,547,459 | A | 8/1996 | Kaufman et al. |
| 5,549,544 | A | 8/1996 | Young et al. |
| 5,556,372 | A | 9/1996 | Talish et al. |
| 5,604,204 | A | 2/1997 | Ammann et al. |
| 5,626,554 | A | 5/1997 | Ryaby et al. |
| 5,656,016 | A | 8/1997 | Ogden et al. |
| 5,656,598 | A | 8/1997 | Dunstan et al. |
| 5,697,976 | A * | 12/1997 | Chesterfield et al. ......... 623/11 |
| 5,730,705 | A | 3/1998 | Talish et al. |
| 5,755,746 | A | 5/1998 | Lifshey et al. |
| 5,759,033 | A * | 6/1998 | Elia ........................... 433/173 |
| 5,762,616 | A | 6/1998 | Talish et al. |
| 5,792,753 | A | 8/1998 | Falk et al. |
| 5,814,604 | A | 9/1998 | Oppermann et al. |
| 5,840,325 | A | 11/1998 | Kuberasampath et al. |
| 6,231,528 | B1 * | 5/2001 | Kaufman et al. .............. 601/2 |
| 6,417,247 | B1 * | 7/2002 | Armstrong et al. ......... 523/115 |

OTHER PUBLICATIONS

James D. Heckman et al., "Acceleration of Tibial Fracture–Healing by Non–Invasive, Low–Intensity Pulsed Ultrasound", *The Journal of Bone and Joint Surgery*, 1994, vol. 76–A, No. 1, pp. 26–34.

W. J. W. Sharrard, "A Double–Blind Trial of Pulsed Electromagnetic Fields for Delayed Union of Tibial Fractures", *The Journal of Bone and Joint Surgery*, 1990, vol. 72–B, No. 3, pp. 347–355.

John M. Wozney et al., "Bone Morphogenetic Protein and Bone Morphogenetic Protein Gene Family in Bone Formation and Repair", *Clinical Orthopaedics and Related Research*, 1998, No. 346, pp. 26–37.

Kati Elima, "Osteoinductive Proteins", *Annals of Medicine* 25, 1993, pp. 395–402.

Mark E. Bolander, "Regulation of Fracture Repair by Growth Factors", *P.S.E.B.M. Growth Factors in Fracture Repair*, 1992, vol. 200, pp. 165–170.

Michael E. Joyce et al., "Transforming Growth Factor–B in the Regulation of Fracture Repair", *The Orthopedic Clinics of North Amrica*, Pathologic Fractures in Metabolic Bone Disease, 1990, vol. 21, No. 1, pp. 199–209.

Stephen B. Trippel, "Growth Factors as Therapeutic Agents", American Academy of Orthopaedic Surgeons, Rosemont, IL, Instructional Course Lectures, vol. 46, 1997, Sec. VIII,. Chapter 44, pp. 473–476.

Stephen B. Trippel et al., "Growth factor Treatment of Disorders of Skeletal Growth", American Academy of Orthopaedic Surgeons, Rosemont, IL, Instructional Course Lectures, vol. 46, 1997, Sec. VIII, Chapter 45, pp. 477–482.

Thomas A. Einhorn et al., "Growth Factor Treatment of Fractures", American Academy of Orthopaedic Surgeons, Rosemont, IL, Instructional Course Lectures, vol. 46, 1997, Sec. VIII, Chapter 46, pp. 483–486.

Richard D. Coutts et al., "Effect of Growth Factors on Cartilage Repair", American Academy of Orthopaedic Surgeons, Rosemont, IL, Instructional Course Lectures, vol. 46, 1997, Sec. VIII, Chapter 47, pp. 487–494.

Gregory R. Mundi, "Growth Factors as Potential Therapeutic Agents in Osteoporosis", American Academy of Orthopaedic Surgeons, Rosement, IL, Instructional Course Lectures, vol. 46, 1997, Sec. VIII, Chapter 48, pp. 495–498.

Stephen B. Trippel, "Growth facotr Actions on Articular Cartilage", *The Journal of Rheumatology*, 1995, vol. 22:1, Suppl. 43, pp. 129–132.

Samir Mitragotri et al., "Ultrasound–Mediated Transdermal Protein Delivery", *Science*, vol. 269, Aug. 11, 1995, pp. 850–853).

Samir Mitragotri et al, "A Mechanistic Study of Ultrasonically–Enhanced Transdermal Drug Delivery", *Journal of Pharmaceutical Sciences*, Jun. 1995, vol. 84, No. 6, pp. 697–706.

\* cited by examiner

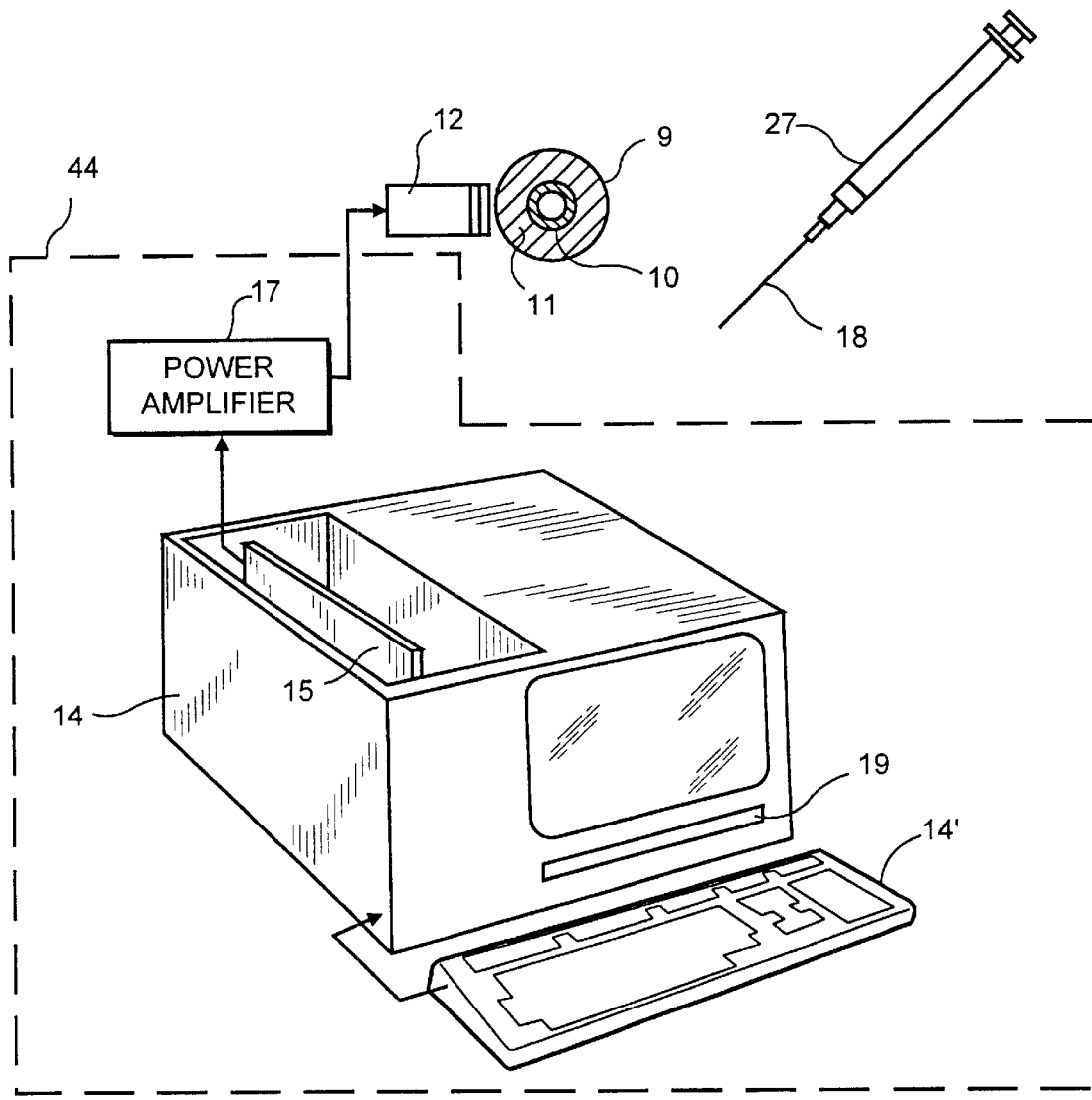
F I G. 1

ULTRASONIC AND GROWTH FACTOR BONE-THERAPY: APPARATUS AND METHOD

This application is a continuation of U.S. patent application Ser. No. 09/232,101 filed Jan. 15, 1999, now U.S. Pat. No. 6,231,528.

FIELD OF THE INVENTION

The invention pertains generally to apparatus and method for therapeutically treating musculoskeletal tissue in vivo. In particular, the invention pertains to the combined use of biophysical and biochemical stimuli for therapeutically treating bone and other musculoskeletal tissue in vivo. More particularly, the invention pertains to the combined use of ultrasound and a bone growth factor for therapeutically treating bone in vivo.

BACKGROUND OF THE INVENTION

In recent years, various attempts have been made to stimulate bone growth. These approaches have not been particularly successful, and as a consequence have not as yet received broad acceptance by either the professional (i.e., medical) or lay (i.e., patient) community. Further, this lack of effectiveness has resulted in a reluctance of the third-party payer community (e.g., insurance companies and HMO's) to offer reimbursement, so that commercialization of such stimulation technologies has been stalled.

A number of issued patents disclose methods and apparatuses to biophysically treat bone and other musculoskeletal tissue. For example, Kaufman et al., U.S. Pat. No. 5,309,808 disclose apparatus and method for therapeutically treating and/or quantitatively evaluating bone tissue in vivo, by subjecting bone to an ultrasonic signal pulse of finite duration, and involving a composite sine-wave signal consisting of plural discrete frequencies. These frequencies are spaced in the ultrasonic region to approximately 2 MHz; the excitation signal is repeated substantially in the range 1 to 1000 Hz. In a closely related patent, Kaufman et al., U.S. Pat. No. 5,458,130, the same inventors extend the apparatus and method to the treatment to musculoskeletal tissue in general. In another patent by the same inventors, Kaufman et al., U.S. Pat. No. 5,547,459 disclose apparatus and method for therapeutically treating bone tissue in vivo, by subjecting bone to an ultrasonic sinusoidal signal pulse peculiarly modulated by a sinusoidal signal with a frequency between about 0 Hz and 25 kHz.

Duarte, U.S. Pat. No. 4,530,360 discloses apparatus and a method of using ultrasonic energy for therapeutic treatment of bone tissue in vivo, using a pulsed sine wave at substantially a single frequency within the range 1.3 to 2.0 MHz, and at a pulse repetition rate of 100 to 1000 Hz.

McLeod et al., U.S. Pat. Nos. 5,103,806 and 5,191,880 disclose methods for promotion of growth bone tissue and the prevention of osteopenia, using mechanical loading of the bone tissue. In both patents, the inventors apply a mechanical load to the bone tissue at a relatively low level on the order of between about 50 and about 500 microstrain, peak to peak, and at a relatively high frequency in the range of about 10 and 50 hertz.

Bassett et al., U.S. Pat. No. 4,928,959 disclose method and device for providing active exercise treatment for a patient suffering from a bone disorder. A patient is subjected to an impact load in order to stimulate bone growth, with an impact load sensor being used to monitor the treatment strength.

Numerous other patents disclose methods for stimulating bone growth relying on the generation of electromagnetic signals. For example, Ryaby et al. U.S. Pat. Nos. 4,105,017 and 4,315,503 describe methods for promoting bone healing in delayed and nonunion bone fractures, using an asymmetric pulsed waveform. In U.S. Pat. No. 4,993,413, McLeod et al. disclose method and apparatus for inducing a current and voltage in living tissue to prevent osteoporosis and to enhance new bone formation. They disclose the use of a symmetrical low frequency and low intensity electromagnetic signal substantially in the range of 1–1000 Hertz. In Liboff et al., U.S. Pat. No. 5,318,551 (and others), methods are disclosed which incorporate the combined use of a static and time-varying magnetic field to stimulate bone healing and growth. Specific amplitudes and frequencies are disclosed for optimal enhancement of bone growth, based on the theory of "ion-cyclotron resonance."

Non-biophysical methods, i.e., methods which use a biochemical compound (or generically a "bone growth factor") to stimulate bone growth have also been described. For example, Ammann et al., U.S. Pat. No. 5,604,204 disclose method for inducing bone growth using a bone growth factor composition known as TGF-$\beta$, in an animal, locally at a bone site where skeletal tissue is deficient. The TGF-$\beta$ is contained in a "pharmaceutically acceptable carrier" in an amount effective to induce bone growth at the bone site.

Dunstan et al., U.S. Pat. No. 5,656,598 disclose method involving therapeutic (biochemical) compositions for the prevention and treatment of pathological conditions involving bone and dental tissue. The invention achieves its objectives by administering a fibroblast growth factor (FGF-1) to an animal or human in need of such treatment.

Oppermann et al., U.S. Pat. Nos. 5,354,557 and 5,814,604, disclose methods involving osteogenic devices. (The use of the term "devices" should be understood to denote a biochemical compound or bone growth factor in an appropriate matrix for delivery to the bone.) The osteogenic devices are comprised of a matrix containing substantially pure naturally-sourced mammalian osteogenic protein. They also disclose DNA and amino acid sequences for novel polypeptide chains useful as subunits of dimeric osteogenic proteins, and methods of using the osteogenic devices to mimic the natural course of endochondral bone formation in mammals. The inventors also disclose methods of producing osteogenic proteins using recombinant DNA technology.

Balazs et al., U.S. Pat. No. 5,128,326, disclose systems based on hyaluronans derivatives, as well as methods for preparing same. Such systems are useful for treatment of cartilage tissue.

Falk et al., U.S. Pat. No. 5,792,753 disclose a pharmaceutical composition which contains a drug that inhibits prostaglandin synthesis, and also contains an amount of a form of hyaluronic acid. The composition is topically administered to the skin and is useful for the treatment of cartilage as it relates to arthritis.

Wang et al., U.S. Pat. No. 5,4,877,864, disclose human and bovine bone and cartilage inductive (biochemical) factors. Such factors may be produced by recombinant techniques and may be useful for treatment of various musculoskeletal tissue defects.

The prior art, exemplified by the references that have been briefly discussed, have used either biophysical or biochemical approaches, to promote bone growth, bone ingrowth and bone healing, or other musculoskeletal tissue healing or growth. In either case, that is, in the biophysical approach (including for example, ultrasound methods), or in the biochemical approach (including, for example, bone growth factors such as TFG-β), treatment has not been effective enough to lead to widespread use. However, the present inventors have discovered how to dramatically enhance the efficacy of such therapeutic methods for bone growth and other musculoskeletal tissue healing, taking advantage of the uniquely synergistic nature associated with the two basic approaches.

BRIEF STATEMENT OF THE INVENTION

It is accordingly an object of the invention to provide an improved method and apparatus for therapeutically treating bone and other musculoskeletal tissue in vivo, whereby to promote bone and other musculoskeletal tissue healing, growth and ingrowth.

Another object is to meet the above object, such that bone and musculoskeletal tissue healing, growth and ingrowth may be more efficiently and more effectively treated than heretofore.

A specific object is to take advantage of the synergistic properties associated with combined application of biochemical and biophysical treatment methods whereby to achieve the indicated objectives.

A further specific object is to take advantage of the synergistic properties associated with biochemical and biophysical treatment methods whereby to achieve much shorter total treatment times, shortening both daily treatment times and the total number of daily treatments required.

A further specific object is to achieve the above objects with a specially chosen set of ultrasonic signals, designed with respect to a mathematical model for evaluating the displacement associated with a biochemical compound.

It is a general object to achieve the foregoing objects with apparatus components that are for the most part commercially available.

Briefly stated, the invention in its presently preferred form achieves the foregoing objectives by injecting through skin overlying a bone to be treated, a biochemical compound containing an osteogenic protein (i.e., a bone growth factor). Soon after this injection, the bone is iteratively subjected to an ultrasonic signal of finite duration, consisting of frequency components in the ultrasonic region to approximately 10 MHz, delivered by a transducer placed on skin overlying the bone; the excitation signal is repeated in the range of 1 to 1000 Hz. The exposure time for ultrasonic therapy is chosen to be in the range of 1 minute to 1 hour, for 1 to 3 times a day, for a period of days as necessary for healing or for promoting bone growth or bone ingrowth. In the presently preferred embodiment of the invention, a single ultrasound treatment lasting for 15 minutes is applied within one hour of the injection of the bone growth factor, and achieves the indicated objectives.

In the currently preferred embodiment, the ultrasonic signal is generated by a pulser to which the transducer is connected. The pulser emits a negative going narrow square pulse of about −300 volts; the duration of the pulse itself is about 0.3 microseconds. The transducer emits an ultrasound signal with a center frequency of about 3 MHz, and of about 1 microsecond in duration, thereby creating a broadband exponentially damped 3 MHz sinusoidal signal. The signal is repeated at a repetition rate of 4,500 Hz.

In the presently preferred embodiment, the ultrasound interacts with the bone growth factor in such a way as to enhance in a positive fashion the bone healing, bone growth and bone ingrowth processes. This combined effect of the ultrasound therapy in the presence of the bone growth factor produces a synergistically enhanced response, namely one that is many times more effective than that which would be produced by having either agent acting alone. In this way, the present invention, besides offering much enhanced bone healing, bone growth and bone ingrowth results, also benefits from significantly shorter treatment periods, both from reductions in the total daily treatment time, but even more importantly, from dramatic reductions in the total number of days required for treatment, which result from application of the methods disclosed herein.

BRIEF DESCRIPTION OF THE DRAWINGS

FIG. 1 is an electrical-circuit diagram schematically showing the interconnected relation of components of apparatus of the invention.

DETAILED DESCRIPTION OF THE INVENTION

Figure 2A:
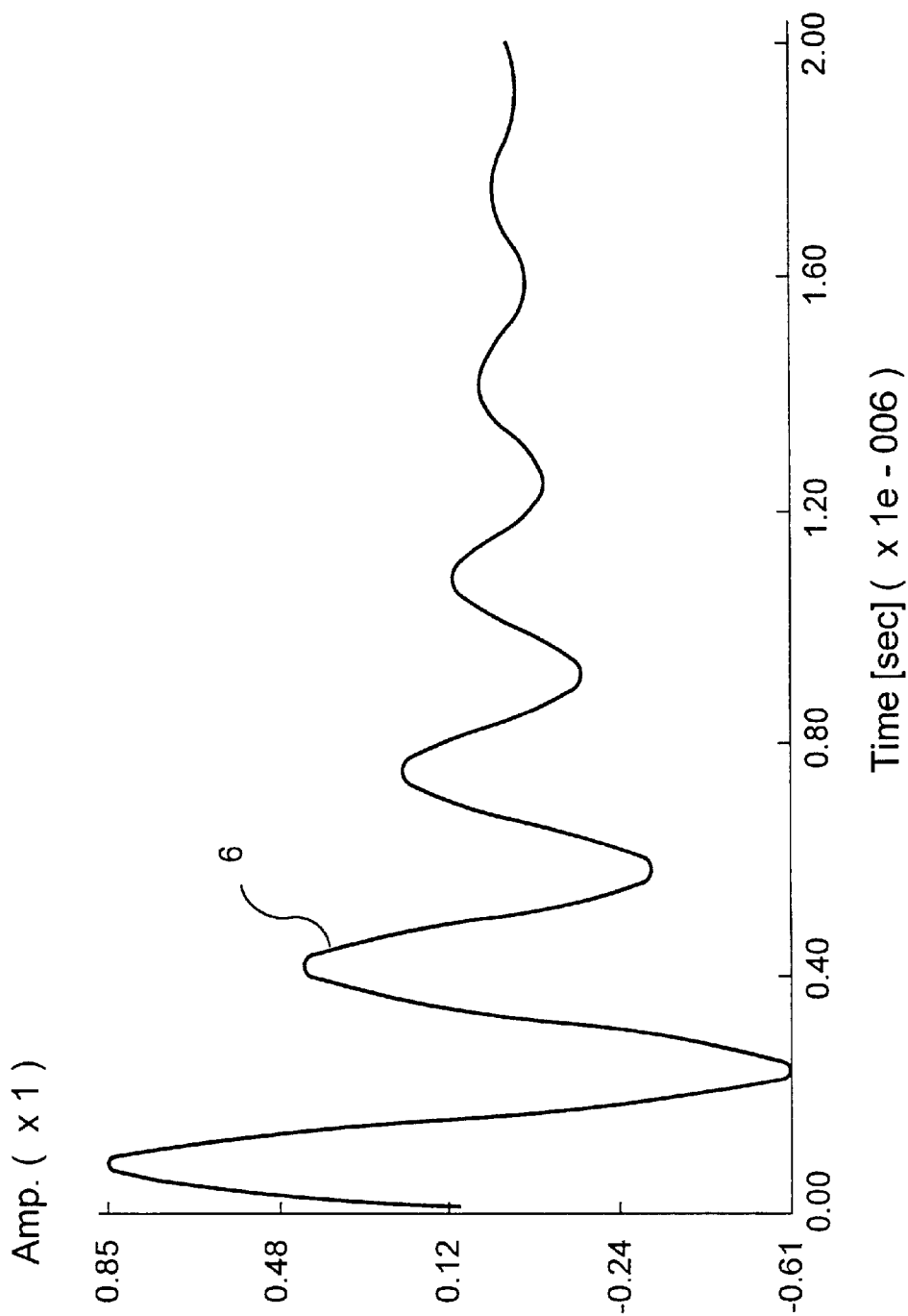
FIG. 2 is a set of acoustic ultrasonic signals used for stimulation of bone growth and healing for several of the currently preferred embodiments.

The invention will be described in detail for a presently preferred embodiment, in conjunction with the accompanying drawings. The invention is shown in FIG. 1 in application to interconnected components for constructing apparatus for performing methods of the invention, namely for therapeutically treating bone in vivo, whereby to stimulate bone growth, bone ingrowth and bone healing. These components are, in general, commercially available from different sources and will be identified before providing detailed description of their total operation.

In FIG. 1, the bone locale 10 to be treated is shown surrounded by soft tissue 11 and skin 9 and to be placed next to an ultrasonic transducer 12, and obtainable from Panametrics, Inc., Waltham, Mass.; suitably, the transducer 12 may be Panametrics "Videoscan" part number V318-SU, having a nominal element size of ¾" diameter, and rated for 1 MHz. As shown, transducer 12 is used for signal launching, in which the launched signal is transmitted through standard ultrasonic couplant (not shown), through the skin, soft tissue and into the bone tissue. The ultrasound couplant may suitably be obtained from Parker Laboratories, Incorporated, of Orange, N.J. In this way the ultrasound transducer may be understood to be acoustically coupled to the skin 9.

Basic operation is governed by computer means 14, which may be a PC computer, such as the "400 MHz Pentium II" available from Gateway 2000, Inc., North Sioux City, S.Dak.; as its designation suggests, this computer contains a 400 MHz clock-pulse generator, and an Intel Pentium II processor, with provision for keyboard instruction at 14'.

An electrical function-generator card 15 is relied upon to generate an excitation signal which is supplied to the launch transducer 12, via power amplifier means 17. The power amplifier is suitably Model No. 240L, an RF power amplifier product of EIN, Inc., Rochester, N.Y. This product provides a 50 dB gain, over the range 20 kHz to 10 MHz.

Figure 3:
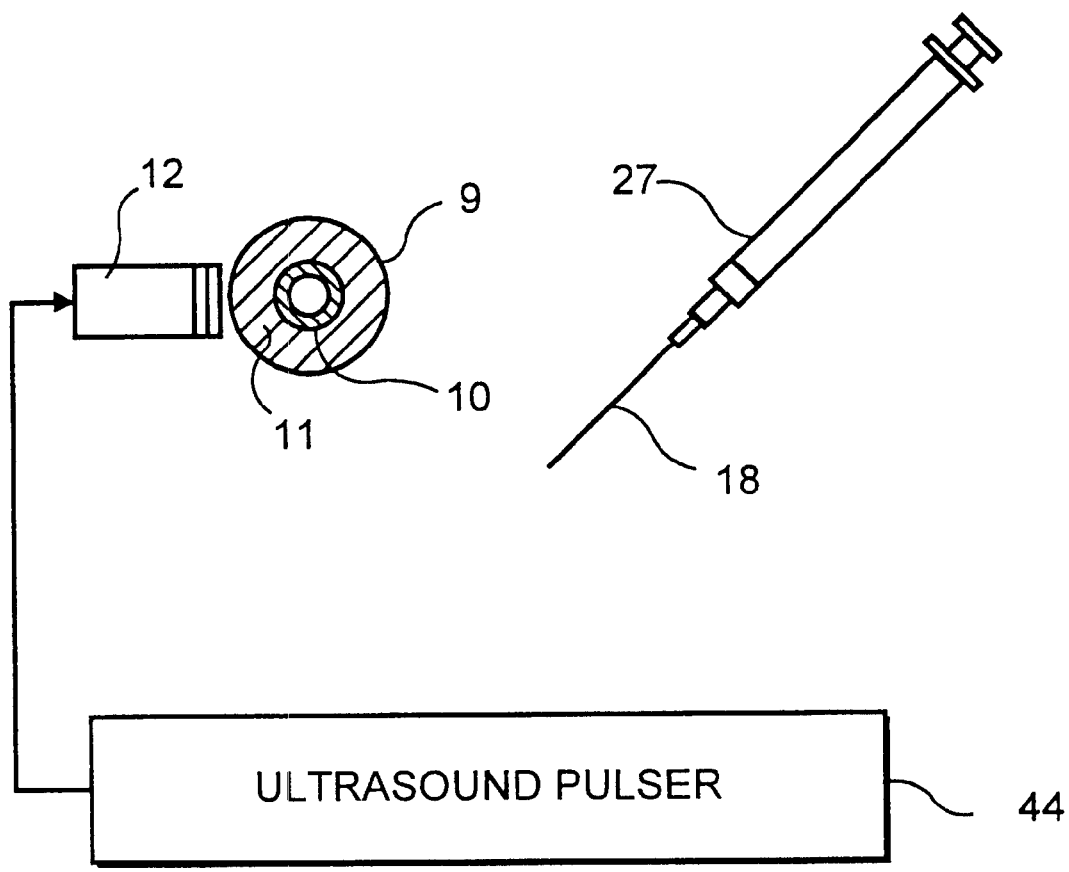
FIG. 3 is an electrical-circuit diagram schematically showing the interconnected relation of components of apparatus of an alternative embodiment of the invention.

The excitation signal generated by card 15 is a negative pulse signal, of about 0.3 seconds in duration; after input of this signal to power amplifier 17, the value of the output signal from the power amplifier 17 is approximately −300 volts. Card 15 may suitably be a waveform synthesizer product of Quatech, Inc., Akron, Ohio, identified by Quatech part No. WSB-100. This waveform synthesizer provides generation of analog signals independent of the host computer 14, allowing full processor power to be used for other tasks, including calculation of waveform data; it has the capacity to generate an output signal comprising literally thousands of points in the indicated frequency range. The computer 14, card 15, and power amplifier 17 may be understood to comprise an ultrasound pulser 44 (shown within the dashed line in FIG. 1); however its present embodiment as described herein has much more flexibility than conventional ultrasound pulsers because of the wide range of electrical excitation signals that may be realized. (It should nevertheless be understood that a conventional ultrasound pulser may also be utilized in the present invention, as shown in FIG. 3.)

A needle syringe 18 is also shown and contains 20 milliliters of a bone growth factor 27. In the presently preferred embodiment of the invention, the bone growth factor 27 is TGF-β. This bone growth factor may suitably be obtained from Genentech, Inc., of South San Francisco, Calif.

Finally, general signal-processing/display/storage software, for the signal processing control and operation of the computer is not shown but will be understood to be a CD-ROM loaded at 19 into the computer; this software is suitably MATLAB 5, available from The MathWorks, Inc., Natick, Mass. Further software, also not shown include the Signal Processing, Optimization and Statistics Toolboxes, also available from MathWorks, as well as C++ Version 5, available from the Microsoft Corporation, Bothell, Wash.

Figure 2B:
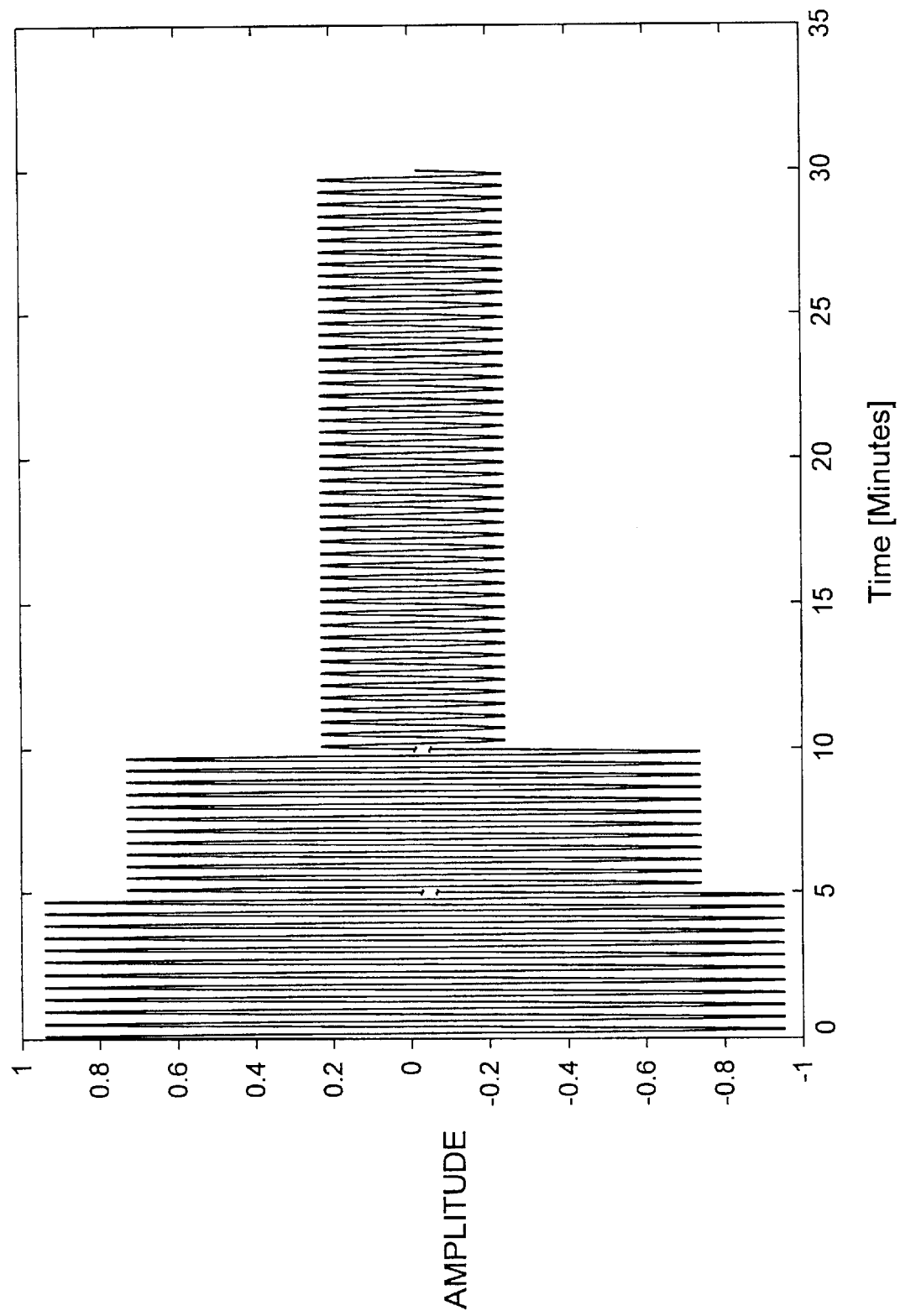

In the presently preferred embodiment of this invention and with additional reference to FIGS. 1 and 2, soft tissue 11 surrounding bone locale 10 is injected through skin 9, with a bone growth factor 27 using syringe 18. An ultrasound transducer 12, connected to an ultrasound pulser 44, is placed next to bone locale 10 with surrounding soft tissue 11 and skin 9, with sufficient ultrasound gel to insure efficient acoustic coupling. An ultrasound signal is transmitted from transducer 12, passes through skin 9, soft tissue 11, and into the bone locale 10. The transmitted ultrasound signal is generated by pulsing the transducer with a 0.3 microsecond duration −300 volt square wave. With particular reference to FIG. 2(A), this produces an ultrasound signal with a center frequency of about 3 MHz, and of about 1 microsecond in duration, thereby creating a broadband exponentially damped 3 MHz sinusoidal signal, 6. This signal is repeated at a frequency of 4,500 Hz.

In the presently preferred embodiment of the invention, the ultrasound signal is applied within 10 minutes of the injection of the bone growth factor, for an initial ultrasound treatment time of 15 minutes. Subsequently, two 15 minute ultrasound treatments per day are applied, for 7 days total. It should be understood that in the presently preferred embodiment subsequent ultrasound treatments are applied without any additional injections of the bone growth factor. In most cases, ultrasound treatments lasting no more than 1 week to 2 weeks will achieve the indicated objectives regarding bone healing, bone growth and bone ingrowth; in many cases, only the single initial ultrasound treatment is required to achieve the indicated objectives.

The preceding description has proceeded on the basis that a biophysical stimulus, that is, ultrasound, when used in conjunction with application of a biochemical compound, that is, a bone growth factor, can dramatically improve the bone healing properties many times over that which would be obtained by using either factor alone. The basis for the above statement is rooted in a fundamental insight which led the present inventors to their current invention. This insight is that ultrasound interacts in such a way as to directly modify the velocities and displacements of the molecules of the biochemical compound. This modification or "stirring" of the bone growth factor molecules, which includes an induced drifting of the molecules towards the surface of the bone, provides a multiplicative enhancement of the direct effects of the ultrasound and bone growth factor when each acts individually. This effect is further enhanced through a small but present local heating phenomenon and associated increase in local blood flow, induced by the ultrasound, that affects in a beneficial way the biochemically treated soft tissue and bone.

It is therefore useful to describe in more detail the basis for the synergistic behavior arising from application of ultrasound in conjunction with use of a bone growth factor. A basic principle of the present invention is that the normal diffusion process of the molecules of a bone growth factor can be enhanced by the external ultrasound exposure. This in turn can produce higher concentrations of the bone growth factor molecules in a shorter time in regions to be treated. It should be further understood that these higher concentrations of bone growth factor lead to increases in the associated binding of the bone growth factors or messengers to their target cells in the bone, and thus to enhanced activity. The enhanced activity may also be produced through an induced microstirring, or displacements induced on the bone growth factor molecules by the external ultrasound. The basic equations for describing the above interactions are given by:

$$M\frac{dv_i}{dt} = M\beta(v_a - v_i) + N \quad (1)$$

and $$\Phi = -D\nabla c + c(v_a - \bar{v}) \quad (2)$$

In Eqs. 1–2, it should be understood that $c=c(x,y,z,t)$ is the concentration of the bone growth factor at time, t, and spatial coordinates (x, y, z) (i.e., the number of bone growth factor molecules per cubic meter at time, t, and spatial coordinates (x, y, z)), $v_i$ is the velocity of the i-th molecule, β is the collision frequency of Langevin, M is the mass of the molecule, $V_a$ is the velocity of the particles of the medium in which the bone growth factor molecules are moving, N is random (thermal) noise force, D is the diffusion coefficient associated with the molecules, $\bar{v}$ is the ensemble mean velocity of the molecules, and Φ is the molecule flux density in units of number of molecules per squared meter second. It should also be understood that $M\beta(v_a-v_i)$ is the individual drag force acting on a single particle, and $M\beta(v_a-\bar{v})$ is the average drag force. The corresponding contribution to the flux density is equal to c·average drag force/$(M\beta)\equiv c$ $(v_a-\bar{v})$. In the case of a spherical molecule (or messenger) of radius, $R_0$, moving in a medium of viscosity, η), then $M\beta=6\Pi\eta R_0$.

The random force contributes to the diffusion a term $-D \nabla c$, where $D=kT/(6\Pi\eta R_0)$, where k is Boltzmann's constant and T is the temperature in degrees Kelvin.

Another relationship which can be obtained from the definition of the molecule flux is:

$$\phi = c\bar{v} \tag{3}$$

Then, equating Eq. 2 with Eq. 3 leads to the following two equations:

$$\bar{V} \cong \frac{V_a}{2} - \frac{D}{2}\nabla \ln c \text{ and} \tag{4}$$

$$\Phi \cong c\frac{V_a}{2} - \frac{D}{2}\nabla c \tag{5}$$

It should be understood that, $v_a$, the acoustic velocity of the medium particles, can be computed from the linear solution of the elastic wave equation. Such a solution is widely known in the art, and a commercial software package even exists for computing it. This software, Wave2000, may suitably be obtained from CyberLogic, Inc., located in New York, N.Y.

Two additional equations required to solve for the concentration $c=c(x,y,z,t)$ of the bone growth factor molecules (or messengers) are the continuity equations:

$$\vec{\nabla} \cdot \Phi = -\frac{\partial c}{\partial t} + K^- c_B - K^+(s - c_B)c \tag{6}$$

$$0 = -\frac{\partial c_B}{\partial t} - K^- c_B + K^+(s - c_B)c \tag{7}$$

In Eqs. 6 and 7, s is assumed to be the concentration of binding sites for the bone growth factor molecules, $c_B$ is assumed to be the volume concentration of bound messengers, and $K^+$ and $K^-$ are the adsorption and desorption rate "coefficients," respectively. Solving Eq. 6 for $c_B$ and substituting it in Eq. 7, the following equation can be derived:

$$(K^- + cK^+)^2\left[\nabla \cdot \Phi + \frac{\partial c}{\partial t}\right] + \left[\frac{\partial}{\partial t}(\nabla \cdot \Phi) + \frac{\partial^2 c}{\partial t^2} + K^+s\frac{\partial c}{\partial t}\right]K^- + \left[\frac{\partial}{\partial t}(\nabla \cdot \Phi) + \frac{\partial^2 c}{\partial t^2}\right]cK^+ - \left[\nabla \cdot \Phi + \frac{\partial c}{\partial t}\right]K^+\frac{\partial c}{\partial t} = 0 \tag{8}$$

Finally, the divergence of the flux, $\nabla \cdot \Phi$, can be expressed as $$\nabla \cdot \Phi = \frac{1}{2}\nabla c \cdot v_a + \frac{1}{2}c\nabla \cdot v_a - \frac{D}{2}\nabla^2 c \tag{9}$$

It should be understood that by substituting Eq. 9 into Eq. 8, a partial differential equation for the concentration of bone growth factor molecules, at time, t, and at spatial coordinates, (x,y,z), is obtained. Solution may be obtained by a number of ways known in the art. In the presently preferred embodiment, the method of finite differences is used. A suitable reference for this technique may be found in the book *Numerical Recipes in FORTRAN The Art of Scientific Programming*, Second Edition, by William H. Press, Saul A. Teukolsky, William T. Vetterling and Brian P. Flannery, published by Cambridge University Press, Cambridge, England in 1992, and which is incorporated by reference hereinto. The concentration, c, and flux, $\Phi$ (as computed according to Eq. 5), are thus affected by an external ultrasound input, through the induced motion of the medium particles, as represented by a non-zero value for $v_a$.

It is to be understood that this results in synergistic enhancements of bone healing, bone growth and bone ingrowth effects.

It is useful to provide further analysis of the basis by which the synergistic behavior with the biophysical and biochemical inputs may be obtained. To do this, a consideration of the one-dimensional case is given. The basic equations then reduce to:

$$\frac{\partial c}{\partial t} = \frac{D}{2}\frac{\partial^2 c}{\partial z^2} - \frac{1}{2}\frac{\partial(v_a c)}{\partial z} \text{ and} \tag{10}$$

$$\Phi = c\frac{v_a}{2} - \frac{D}{2}\frac{\partial c}{\partial z} \tag{11}$$

Therefore, in the one-dimensional case, and with the further simplifying assumptions that $K^+=K^-=s=0$, the concentration, c, of the molecules of the bone growth factor is obtained by solving Eq. 10. Eq. 11 may then be solved for the molecule flux, $\Phi$, in the presence ($v_a \neq 0$) and in the absence ($v_a = 0$) of ultrasound exposure.

It should be further pointed out that the external ultrasound waveform is responsible for inducing motion of the particles of the propagation medium (i.e., the soft tissue and bone), as represented through the velocity, $v_a$. It is this particle motion that gives rise to the enhanced effects of the combined stimulations, through the non-linear interactions with the bone growth factor molecules. Thus, different ultrasound waveforms will in general give rise to distinct effects in terms of the bone healing, bone growth and bone ingrowth. It has been pointed out supra that algorithms (i.e., computer software) exist for the evaluation of the induced medium particle velocity. Alternatively, under some simplifying assumptions, analytic expressions for the medium velocity, $v_a$, may also be described. One such example is given by $$v_a = v_0 e^{-\alpha z}\sin\omega\left(t - \frac{z}{v_p}\right) \tag{12}$$

In Eq. 12, $v_0$ is the induced particle motion of the medium (i.e., soft tissue) at the surface (i.e., the outer layer of the skin), $\alpha$ is the attenuation of the medium, $\omega$ is the radian frequency, z is the depth at which the velocity is being evaluated and $z=0$ is the outer skin surface, and $v_p$ is the velocity of the ultrasound wave within the medium. It should be appreciated that in this characterization any discontinuities in the medium have been ignored, i.e., a semi-infinite uniform half-space is assumed.

Yet another example of a particle velocity, $v_a$, is given by $$v_a = v_0 e^{-\alpha z}\sum_{n=0}^{\infty} f\left(t - nT - \frac{z}{v_g}\right) \tag{13}$$

In Eq. 13, 1/T is the repetition rate of the signal waveform, f(.), and $v_g$ is the group velocity of the ultrasound wave. In the case of no dispersion, the group velocity, $v_g$, is equal to the phase velocity, $v_p$. In cases of dispersion, the value of the group velocity, $v_g$, may most suitably be chosen to be at the nominal center frequency of the waveform, $f(.)$. It should be understood, however, that in the characterization as described in Eq. 13, the dispersion is assumed to be negligible. In other cases, it may be most suitable to compute the full solution to the elastic wave equation, as disclosed supra, in order to evaluate the particle velocity at any point in the medium. It should be understood that any functional description for the ultrasound waveform, $f(.)$, can be utilized in the present invention. In the presently preferred embodiment, $f(.)$ is an exponentially damped sinusoid of 3 MHz, repeating at 4.5 kHz=1/T. However, any waveform, including but not limited to continuous sine, pulsed sine, broadband finite-duration, as well as amplitude and frequency modulated ultrasound signals can be utilized in realizing the objectives of the invention.

It should also be pointed out that in the case of a semi-infinite or infinite medium, the value of $v_0$ can be computed from the following expression:

$$I_a = \frac{1}{2} \rho_d v_p v_0^2 \tag{14}$$

In Eq. 14, $\rho_d$ is the medium (tissue) density, and $I_a$ is the acoustic (ultrasound) power intensity in Watts per square meter that enters the tissue at z=0, that is, that enters the skin surface. An excellent reference for explaining the relationship between acoustic intensity and medium velocity may be found in the book entitled *Physical Principles of Medical Ultrasonics*, by C. R. Hill, published by Halsted Press, New York, in 1986, and which is incorporated by reference hereinto.

The preceding has described an analytic basis for the synergistic effects which are induced by combined application of ultrasound and biochemical compounds, as discovered by the present inventors. It should be further appreciated that other mechanisms by which the ultrasound imput can dramatically enhance the activity of the bone growth factor exist as well. As one such example, the external ultrasound input can affect directly the binding constants $K^+$ and $K^-$, leading to enhanced bone healing results. Additionally, increased local blood circulation due to application of ultrasound can significantly improve the bone healing, bone growth and bone ingrowth effects of a bone growth factor. An excellent reference for these effects induced on blood flow and temperature can be found in the book *Therapeutic Heat and Cold, Fourth Edition*, edited by Justus F. Lehmann and published by Williams and Wilkins of Baltimore, Md. in 1990, and incorporated by reference hereinto. It should be understood that it is the combination of ultrasound with bone growth factors that produces the enhanced bone healing, bone growth and bone growth results.

Another embodiment of the invention involves the combined use of ultrasound with skin surface application of a bone growth factor, for treating a bone fracture. In this embodiment, the bone growth factor is not injected through the skin; instead, it is non-invasively applied to the skin surface overlying the bone to be treated. The ultrasound transducer is immediately placed onto the skin where the bone growth factor was applied, and energized by the ultrasound pulser. Thus it should be understood that a prescribed amount of a biochemical compound is placed on the skin overlying the bone to be treated in a living body, and that the ultrasound transducer, connected to an ultrasound pulser, is acoustically coupled to the skin and produces an ultrasound signal within the bone. In this embodiment of the invention, the applied ultrasound, through the mechanism as described hereinabove, i.e., through the effects on diffusion of the bone growth factor molecules, serves to transfer or transport the bone growth factor through the skin and soft tissue and deliver it to the bone to be treated. In this alternative embodiment of the invention, and with additional reference to FIG. 2(B), a specially designed ultrasound signal is utilized for the first ultrasound treatment, that is the ultrasound treatment immediately after the bone growth factor is applied to the skin outer surface. The ultrasound signal consists of a relatively high intensity 250 mW/cm² (SATA) continuous sinusoid of approximately 1 MHz frequency applied for 5 minutes, and then followed for an additional 5 minutes at 150 mW/cm² (SATA), and ending with 20 additional minutes at 15 mW/cm² (SATA). Subsequent ultrasound treatments are carried out using the 15 mW/cm² (SATA) continuous sinusoid at 1 MHz frequency for 20 minutes two times per day for 2 weeks total. The selected ultrasound signal serves to both transport the bone growth factor through the skin and to synergistically enhance its associated bioactivity and bioeffectiveness. It should therefore be understood that in addition to the transporting of the bone growth factor through the skin, that this embodiment also has associated with it synergistic enhancements in the healing effects, as described hereinabove for the embodiment of the invention in which the bone growth factor was injected through the skin. In this alternative embodiment, injection by syringe or any other invasive means is avoided; the bone growth factor is "pushed" or "conveyed" through the intact skin to the bone. Further, synergistic enhanced response is also realized by the action of the ultrasound in conjunction with the bone growth factor, not only through direct effects on diffusion, but also through associated local increases in blood flow, temperature increases, as well as effects on the adsorption and desorption rate coefficients.

It should be appreciated that although ultrasound is one biophysical stimulus that can synergistically interact with and enhance the bioeffectiveness of a bone growth factor, other biophysical stimuli also can be utilized. In one such alternative embodiment of the invention, acoustic energy, but not ultrasonic, i.e., mechanical energy having only frequencies below approximately 20,000 cycles per second, is used to stimulate bone growth. In this alternative embodiment, a vibrating platform is used to generate dynamic displacements in bone tissue throughout the body. Such a vibrating platform is well known in the art, and may suitably be Model No. 4060-15, obtainable from the Bertec Corporation, of Columbus, Ohio. This model is capable of producing vertical displacements having a frequency content of up to 1800 Hz. This biophysical input, that is a mechanical input having sub-ultrasonic frequency components, has been previously described to have osteogenic capabilities, that is to promote bone healing, growth and ingrowth. An example of such a method is given in the two patents by McLeod et al., U.S. Pat. Nos. 5,103,806 and 5,191,880, which are incorporated by reference hereinto. In these patents, the inventors disclose methods for promotion of growth of bone tissue and the prevention of osteopenia, using mechanical loading of the bone tissue. In the present alternative embodiment of the invention, the effects of the biophysical (i.e., mechanical) input are dramatically enhanced by combining this treatment with a biochemical one, namely, a therapeutic drug. In this alternative embodiment, the drug may suitably be Fosamax, available from Merck & Co., Inc., Whitehouse Station, N.J. It should be understood that in this embodiment both the biophysical (i.e., mechanical) and biochemical (i.e., drug) inputs are systemically applied. Thus, the synergistically enhanced response occurs throughout the skeleton, and most importantly the therapeutic benefit includes, but is not limited to, the hips and spine. In the present embodiment of the invention, the mechanical stimulus is applied for about 10 minutes twice a week, ideally about 2 hours after ingestion by the patient of his or her first Fosamax dose that morning; the benefits obtained under the prescribed regimen are much more dramatic increases in bone mass and marked reductions in bone loss, as well as significant reductions in the total number of biophysical (i.e., mechanical) treatments required per week and reductions by half in the required dosage of Fosamax, in contrast to that which is required without synergistic biochemical and biophysical treatment. The reduction in drug dosage is particularly beneficial as it reduces the potential for side-effects.

Although in the alternative embodiment of the invention as disclosed in the preceding paragraph, mechanical energy (that is, vibrations inducing displacements and strains) was combined with biochemical treatment with Fosamax, it should be understood that any drug which stimulates bone growth, or inhibits bone loss, or acts on both such aspects of bone physiology and metabolism, may be utilized. Such drugs can include any biochemical compound, such as estrogen or estrogen-like compounds, bisphophonates, calcitonins, fluorides, anabolic bone agents, anti-resorptive drugs, selective estrogen receptor modulators, PTH or other therapeutic peptides, or any bone growth factor. It should be further understood that although in the present alternative embodiment of the invention as described in the preceding paragraph that the biophysical input (i.e., mechanical force) and biochemical compound (i.e., drug) are both systemically applied, local treatments are also considered to be within the scope of the present invention. The local nature of the treatments can be understood to be associated with either the mechanical stimulus or the biochemical stimulus, or with both. The synergistic effects due to the externally induced vibratory motion of the bone and soft tissue in combination with application of the biochemical compound are responsible for the enhanced bone healing, bone growth and bone ingrowth results. It should therefore be additionally understood that a variety of mechanical stimulation methods may be utilized in alternative embodiments of the present invention. For example, another method and apparatus for generating mechanical energy in a living body is described by Bassett et al., U.S. Pat. No. 4,928,959 and which is incorporated by reference hereinto; they disclose method and device for providing active exercise treatment for a patient suffering from a bone disorder, in which a patient is subjected to an impact load in order to stimulate bone growth, with an impact load sensor being used to monitor the treatment strength. Such methods also benefit greatly from their synergistic combination with biochemical compounds according to the invention as disclosed herein.

While the alternative embodiments as described in the preceding two paragraphs have focussed on the combined use of mechanical energy at sub-ultrasonic frequencies with biochemical compounds for treating bone loss (as in osteoporosis or osteopenia), bone fracture healing can be treated as well. Thus, in yet a further alternative embodiment of the invention, bone fracture healing is therapeutically treated by combining a mechanical stimulus together with a bone growth factor. In the present embodiment, a bone fixator enabled with "dynamization" is used to treat a bone fracture. Dynamization is a method by which a certain amount of mechanical energy is provided to a bone fracture site, in an effort to accelerate or otherwise optimize the healing process. An apparatus for providing such stimuli to a bone fracture is disclosed in a patent by Faccioli et al., U.S. Pat. No. 5,320,622, and which is included by reference hereinto. In the present embodiment, a fibroblast growth factor, FGF-1, is injected into the fracture site preferably within 5 days of the occurrence of the fracture, and mechanical stimulation via dynamization is applied continuously starting 5 additional days after application of the bone growth factor. The bone growth factor, FGF-1, is suitably available from Rhone-Poulenc Rorer Pharmaceuticals, Inc., of Collegeville, Pa. In the present embodiment, bone healing at the fracture site is significantly enhanced due to the synergistic interaction of the combined application of mechanical stimulation and bone growth factor.

It should be further understood that mechanical stimulation at a fracture site can be achieved not just with "dynamization" as described in the preceding paragraph, but also with induced localized vibrations, as for example with a dynamic vibration shaker, or by induced systemic vibrations, as for example with a vibrating platform; in either case, the vibrations are to be understood to be applied in conjunction with use of a bone growth factor, in order to achieve the objectives of enhanced bone healing and bone growth. For example, in one yet additional alternative embodiment of the invention, a vibration shaker generates relatively high frequency local displacements in a fractured limb. Such a vibration shaker may suitably be Model No. V-102, available from Ling Dynamic Systems, Inc., of Yalesville, Conn. This shaker can generate mechanical vibrations at frequencies of more than 1000 Hertz, and in conjunction with application of a locally applied bone growth factor, can dramatically enhance the fracture healing process, over that obtainable with application of either stimuli individually. In this present alternative embodiment of the invention, the bone growth factor is FGF-1, suitably available from Rhone-Poulenc Rorer Pharmaceuticals, Inc., of Collegeville, Pa.

Figure 4:
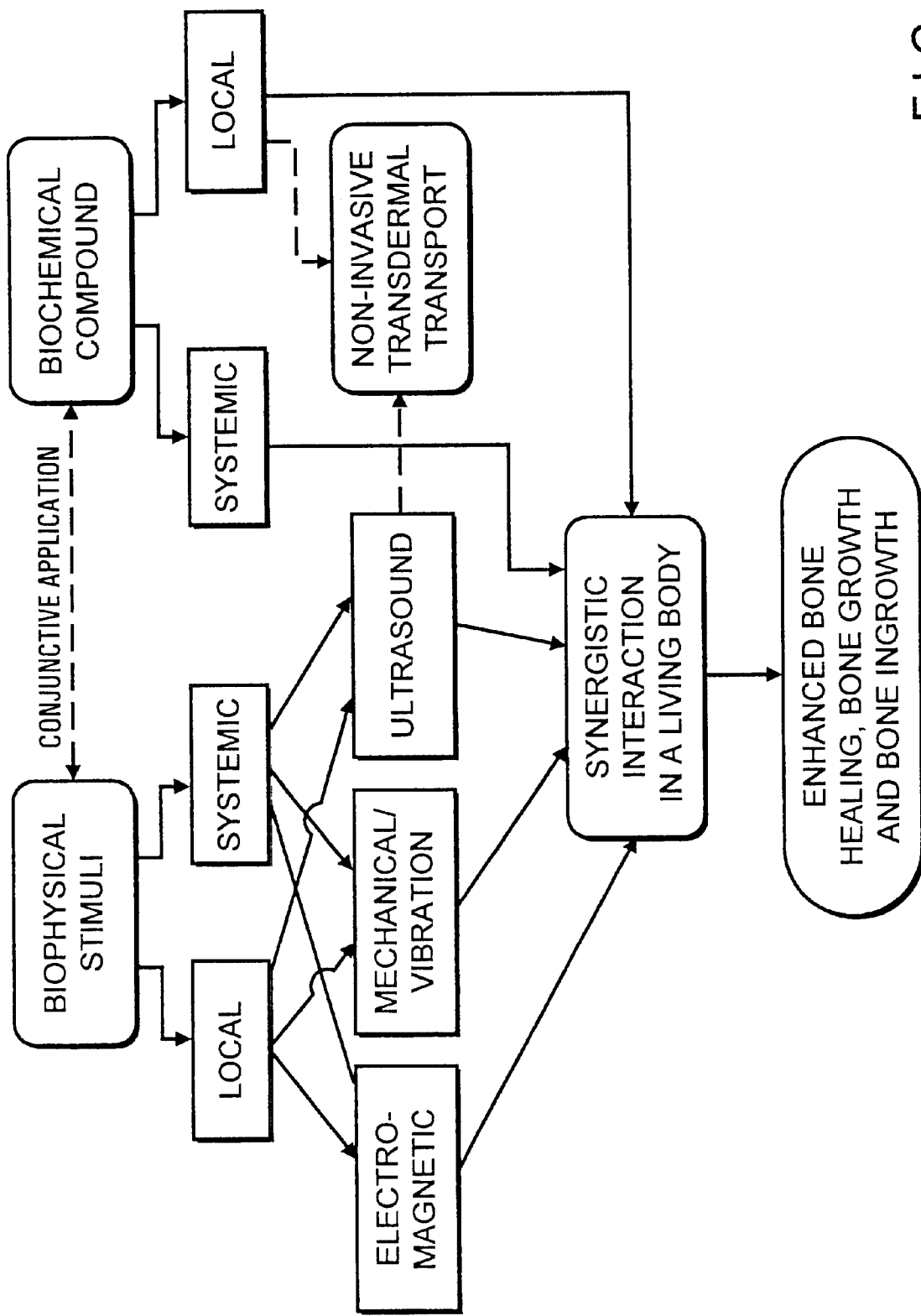
FIG. 4 is a schematic diagram illustrating the interrelationships of several alternative embodiments of the invention.

With additional reference to FIG. 4, it should thus be understood that mechanical (i.e., acoustic, vibrational) stimulation, either at ultrasonic or below ultrasonic frequencies, whether applied locally or systemically, when used in conjunction or combination with a biochemical compound (i.e., a bone growth factor), whether applied locally or systemically (including topical skin application or injection), can dramatically and significantly enhance the bone healing, bone growth and bone ingrowth processes, through a powerful synergistic interaction, as discovered by the present inventors. It should additionally be understood that such methods and apparatti can find use not only in bone fracture healing (in fresh, delayed and non-union fractures) and in treatment for osteoporosis and osteopenia, but also for treatment in the case of orthopaedic implants, for example to promote bone ingrowth around an artificial hip or knee. The disclosed invention can also find use for promoting osteoconduction and osteoinduction around not only orthopaedic implants, but for incorporation of bone grafts as well. Such bone grafts include but are not limited to autologous, bone bank, collagen based, as well as non-bone graft materials. It should be understood that the bone graft materials may be treated directly with a bone growth factor, before being placed into a patient. Subsequently, ultrasound treatment is used to synergistically enhance the amount of bone ingrowth into and around the biochemically treated implant. In one such alternative embodiment of the invention, a non-bone graft material, most suitably Pro Osteon 500R, available from Interpore Cross International of Irvine, Calif., is treated first with an autologous bone growth factor, suitably platelet-derived growth factor, and surgically implanted into the patient. A low intensity (20 mW/cm$^2$ SATA) ultrasound continuous sine signal at 3 MHz is then applied every other day for thirty minutes for a period of 3 weeks. The effect of the growth factor in combination with the ultrasound results in dramatically enhanced bone ingrowth, biomechanical stability and resorption of the non-bone graft material. A related but alternative embodiment of the invention utilizes a bone graft substitute known as NOVOS, suitably available from Stryker Biotech, of Natick, Mass. NOVOS contains type I bone collagen and Osteogenic Protein-1 (OP-1), and, in this alternative embodiment, is surgically implanted into a non-union fracture. The osteogenic proteins are described by Kuberasampath et al., U.S. Pat. No. 5,840,325, which is incorporated by reference hereinto. A low intensity (20 mW/cm$^2$ SATA) ultrasound continuous sine signal at 3 MHz is then applied every other day for thirty minutes, starting within 24 hours from the time of the implant, for a period of 3 weeks. The combination of the ultrasound with OP-1 treated collagen (i.e., NOVOS) results in dramatically enhanced bone healing and consolidation at the fracture site.

As yet one further embodiment of the invention, electromagnetic field ("EMF") energy is used as a biophysical input, in synergistic conjunction with a bone growth factor. In this alternative embodiment, mechanical energy is not employed; instead, an electromagnetic applicator is used to treat a bone which is also treated with a bone growth factor. The electromagnetic applicator is most suitably a "pulsed electromagnetic field ("PEMF") applicator, as available from Orthofix International N.V., located in Curacao, Netherlands; this applicator is described by Erickson et al., U.S. Pat. No. 5,195,941, and which is included by reference hereinto. (In this embodiment, and with additional reference to FIG. 4, it is to be understood that the ultrasound transducer and ultrasound pulser shown in FIG. 1 are replaced by the PEMF stimulator.) In this alternative embodiment, TGF-β is injected with a syringe into the soft tissue overlying a non-union bone fracture. The PEMF applicator is applied to the fractured limb on the same day, within 1 hour of the injection of the bone growth factor, for a total treatment time of 1.5 hours. Subsequently, the PEMF is applied daily for 1.5 hours for approximately 2 weeks, in order that healing of the non-union may be stimulated sufficiently to go on to heal fully, through the synergistic interaction of the external electromagnetic field (i.e., the PEMF) with the bone growth factor (i.e., the TGF-β). It should be understood that the synergistic bone healing response is achieved, in the case of electromagnetic stimulation, largely through direct effects on the K$^+$ and K$^-$ adsorption and desorption rate coefficients, respectively; however, effects on diffusion and blood flow also are mechanisms through which enhanced effects on bone healing, bone growth and bone ingrowth occur. It should be further appreciated that any type of electromagnetic field applicator or signal may be utilized in conjunction with application of a bone growth factor, each either locally or systemically applied. The electromagnetic field energy may further be understood to be applied either inductively, capacitively or through electrodes in contact with the living body.

It should be appreciated that the various biophysical modalities, that is, ultrasonic, mechanical (at sub-ultrasonic frequencies) and electromagnetic energies, can be utilized with a variety of signal waveforms (i.e., temporal characteristics), including continuous sinusoid, pulsed sinusoid, broadband repetitive pulses; and amplitude-modulated and frequency-modulated waveforms. It is, however, to be understood that such application of biophysical signals with specific temporal characteristics are to be utilized in conjunction with a biochemical compound or bone growth factor in order that the indicated objectives can be achieved. It should also be appreciated that the biochemical compound may often be contained in a convenient matrix which is biocompatible and which is used as a "vehicle" to carry the "active" bone growth factor or component. As one such example, TGF-β may be mixed with a basic ultrasound couplant or gel, and the mixture applied to the skin. The gel or matrix serves a dual purpose in this case: (i) as a convenient means to maintain the growth factor in a confined region; and (ii) to efficiently couple the ultrasound signal from an ultrasound transducer to the skin.

While the previously disclosed embodiments of the invention have focused on enhancing bone healing, bone growth and bone ingrowth, it should nevertheless be understood that the methods disclosed herein can find therapeutic application not only to bone but to other musculoskeletal tissues as well. For example, in an alternative embodiment of the invention, osteoarthritis at the knee is treated through the combined application of ultrasound with a biochemical compound. In the present alternative embodiment, and with additional reference to FIG. 1, a 3.5 MHz continuous sinusoidal signal having a spatial-average temporal-average power intensity of 15 mW/cm$^2$ is applied to the skin overlying the knee to be treated. In FIG. 1, the cartilage is not shown but understood to be adjacent to bone 10. In the present embodiment, the biochemical compound is most suitably Synvisc, available from Biomatrix, Inc., of Ridgefield, N.J. It should be understood that Synvisc is injected into the cartilage of the knee to be treated using syringe 18. The knee is then treated with ultrasound, which together with the biochemical treatment (that is, the Synvisc), leads to significantly enhanced reductions in pain and improved function, as compared with that obtained using either (i.e., the ultrasound or biochemical) treatment alone. In the presently preferred alternative embodiment, only one ultrasound treatment (that is, one treatment in conjunction with only one injection of Synvisc) is used, with dramatic improvements in pain relief and function achieved.

It should therefore be understood that all of the previous variations of the invention as disclosed hereinabove for applications to bone apply as well to musculoskeletal tissue in general. Therefore, and with additional reference to FIG. 5, application of a biophysical stimulus or input in conjunction with application of a prescribed amount of a biochemical compound to a living body can be understood to lead to synergistically enhanced musculoskeletal tissue healing, growth and repair. Further, it should be appreciated that the musculoskeletal tissue can include not only bone, but ligament, tendon and cartilage, as well. Moreover, the biophysical stimulus can be applied locally or systemically, and be of either electromagnetic field energy or mechanical energy at sub-ultrasonic frequencies (i.e., vibrational) or at ultrasonic frequencies. The biochemical compound can itself be applied locally or systemically as well (e.g., be injected through or topically applied to the skin), and can be understood to be comprised of any substance or class of substances that can interact biochemically with the musculoskeletal tissue to be treated. This interaction is enhanced synergistically through application of the biophysical stimulus, through effects on diffusion, blood flow, temperature and adsorption and desorption rate coefficients, as described hereinabove. It should also be generally appreciated that the amount of biochemical compound prescribed will be a function of the type of compound and the particular therapeutic application; however, amounts utilized are generally much less when biophysical inputs are employed according to the methods as disclosed herein, in comparison to that required when biochemical compounds alone are utilized.

Figure 5:
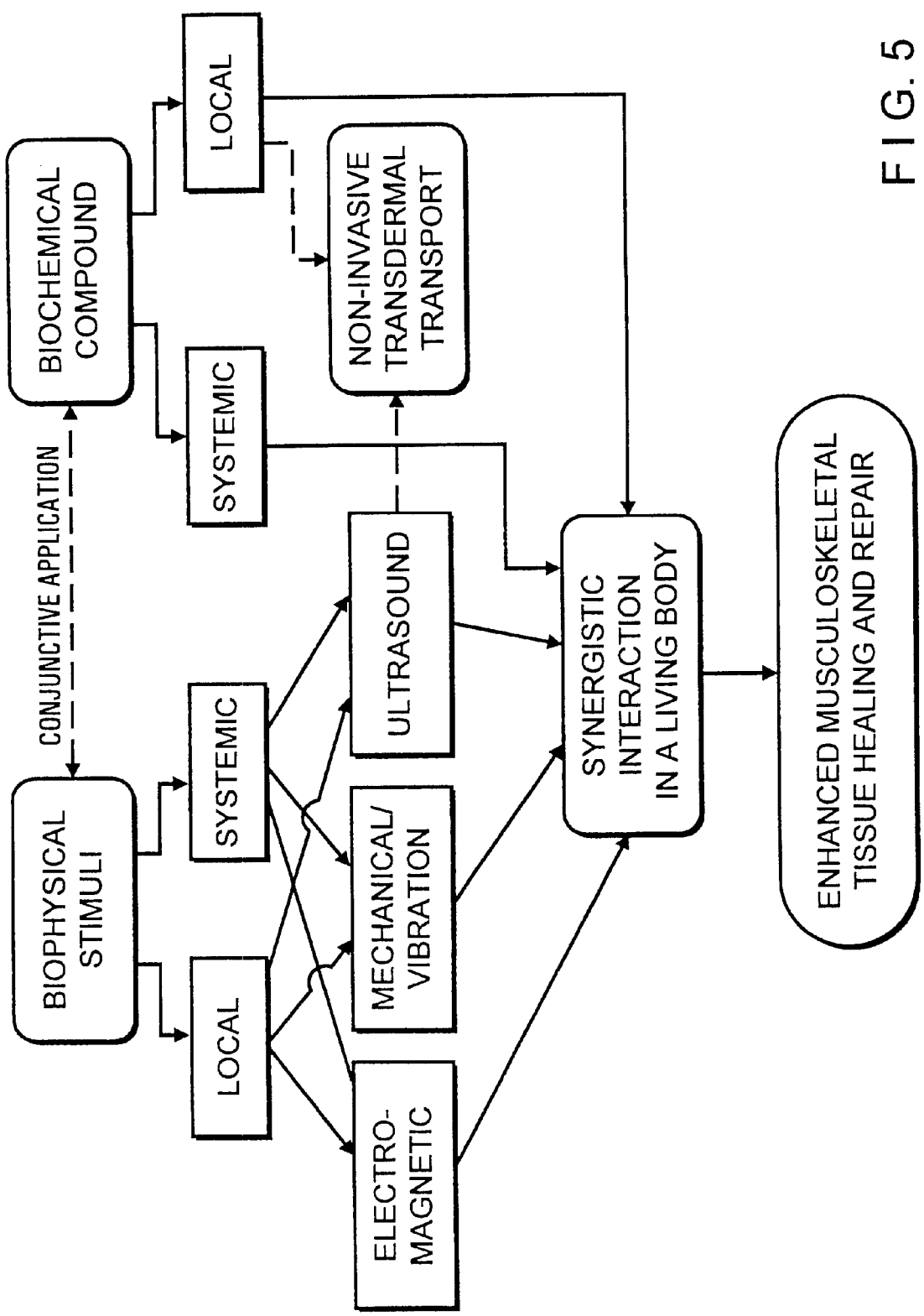
FIG. 5 is another schematic diagram illustrating the interrelationships of several other alternative embodiments of the invention.

With additional reference to FIG. 5, and in particular to the portion shown by the dashed arrows, it should be understood that the application of a biochemical compound to the musculoskeletal tissue, i.e., to bone, ligament, cartilage or tendon, can also be achieved non-invasively by concurrent application of ultrasound. In such an alternative embodiment, a prescribed amount of a biochemical compound is applied to the skin; that is, a prescribed amount of the biochemical compound is placed on the skin overlying the musculoskeletal tissue to be treated. An ultrasound transducer is then acoustically coupled to the skin overlying the musculoskeletal tissue to be treated, and connected to an ultrasound pulser, so that an ultrasound signal is produced within the musculoskeletal tissue. The action of the ultrasound causes the biochemical compound to be transported to the musculoskeletal tissue being treated, without the need for invasive needle injection. Additionally, the ultrasound interacts in a synergistic fashion with the biochemical compound to obtain enhanced therapeutic effects on the musculoskeletal tissue.

Finally, it is important to emphasize that the disclosed invention and its various embodiments rely on the concurrent use of a biophysical stimulus with a biochemical one. This concurrent or conjunctive use is a crucial aspect of the present invention, as it is the basis by which the indicated objectives of synergistically enhanced musculoskeletal tissue healing and growth are achieved. It should be further appreciated that such concurrent or conjunctive use of the biophysical and biochemical stimuli in the context of the current invention may be carried out in a number of ways. For example, the biophysical stimuli can be applied almost immediately (e.g., within several minutes) after the biochemical compound is injected, ingested or otherwise utilized. Alternatively, the biophysical stimuli can be applied after a more significant period of time has elapsed after utilization or application of the biochemical compound. However, the best results are obtained when the biophysical stimulus is applied within twenty-four (24) hours after application of the biochemical treatment. However, good results are also obtained when the biophysical stimulus is applied as many as three (3) months after application of the biochemical treatment. Thus the present invention should be understood to include both long and short time periods between application of the biochemical compound and subsequent application or applications of the biophysical stimuli, so that the meaning of the terms "concurrent," "conjunctive," "combined with" or "in combination with" should be understood in this relatively broad sense. It should lastly be additionally understood that "pre-biochemical treatment" with a biophysical stimuli, that is, application of the biophysical stimulus before utilization of a biochemical stimuli, which serves to "condition" the musculoskeletal tissue, in addition to "post-biochemical treatment" with a biophysical stimuli, can lead to enhanced musculoskeletal tissue healing and growth as well.

While several embodiments of the present invention have been disclosed hereinabove, it is to be understood that these embodiments are given by example only and not in a limiting sense. Those skilled in the art may make various modifications and additions to the preferred embodiments chosen to illustrate the invention without departing from the spirit and scope of the present contribution to the art. Accordingly, it is to be realized that the patent protection sought and to be afforded hereby shall be deemed to extend to the subject matter claimed and all equivalence thereof fairly within the scope of the invention.

It will be seen that the described invention meets all stated objectives as to therapeutic treatment in vivo of bone tissue specifically and musculoskeletal tissue in general, with specific advantages that include but are not limited to the following:

(1) Significantly enhanced healing effects due to the concurrent use of a biophysical stimulus with a biochemical stimulus;

(2) Capability to avoid invasive (e.g., needle injection) for delivery of bone growth and other biochemical factors to the treated musculoskeletal tissue;

(3) Achievement of a dramatic reduction in the required treatment, including both in terms of number of minutes per treatment and even more importantly also the number of total treatments required;

(4) Synergistic response due to the conjunctive use of a biophysical and biochemical stimuli, leading to much more enhanced effects over that which would be obtained using only one of the stimuli;

(5) Description of specific biophysical stimuli, including ultrasonic, mechanical and electromagnetic, that may be used to achieve dramatically enhanced healing and growth, when used in conjunction with a biochemical compound;

(6) Description of a mathematical model to characterize the synergistic interaction of ultrasonic and biochemical stimuli, which may be used in the design of signals with maximal healing effects;

(7) The convenience and practicality of a much more effective method for therapeutically treating bone and other musculoskeletal tissue, allowing in many cases even one single combined application/treatment to achieve the indicated objectives;

(8) Reduction in the potential for side-effects from drugs, because of the smaller doses typically required;

(9) Greater acceptance by the medical and patient communities, and also by third-party-payers, because of its enhanced effectiveness; and

(10) The nature of the apparatus as described here serves best the purposes of further exploration for obtaining maximally effective signals and dosage regimens that can be correlated for the indicated objectives. The embodiments of the invention as described above can explore a wide range of experimental configurations. Their use is expected to lead to the development of compact and efficient apparatus for obtaining the indicated objectives. For example, a compact electronic analog implementation can easily be constructed if economy and simplicity are the primary objectives. Other systems which rely on combined analog and digital electronics are more expensive, yet can be more flexible in terms of the range of applications which can be addressed (e.g., systems for a single therapeutic application to bone fracture healing, versus systems for therapeutic applications to a variety of musculoskeletal tissues and disorders). Further, systems can either be built as a stand-alone unit or as part of a PC-based system.

What is claimed is:

1. A method of therapeutically treating bone tissue in a living body, the method comprising the steps of:
    (a) applying a prescribed amount of a bone growth factor to a bone graft material;
    (b) surgically implanting said bone graft material including said bone growth factor within said bone tissue in said living body;
    (c) applying an ultrasound stimulus to said bone tissue in said living body, wherein said bone tissue includes said bone graft material; and
    (d) exposing said bone tissue to said ultrasound stimulus in conjunction with said bone growth factor for a prescribed period of time,
    to produce a nonlinear interaction between said bone tissue, said ultrasound stimulus, and said bone growth factor, and
    to thereby synergistically promote bone tissue healing, growth, ingrowth and repair.

2. A method of therapeutically treating bone tissue in a living body, the method comprising the steps of:
    (a) applying a prescribed amount of a bone growth factor to an orthopaedic implant;
    (b) surgically implanting said orthopaedic implant including said bone growth factor within said bone tissue in said living body;
    (c) applying an ultrasound stimulus to said bone tissue in said living body, wherein said bone tissue includes said orthopaedic implant; and
    (d) exposing said bone tissue to said ultrasound stimulus in conjunction with said bone growth factor for a prescribed period of time,
    to produce a nonlinear interaction between said bone tissue, said ultrasound stimulus, and said bone growth factor, and
    to thereby synergistically promote bone tissue healing, growth, ingrowth and repair.

3. A method of therapeutically treating bone tissue in a living body, the method comprising the steps of:
    (a) applying a prescribed amount of a bone growth factor to a bone graft material;
    (b) surgically implanting said bone graft material including said bone growth factor within said bone tissue in said living body;
    (c) applying a mechanical stimulus at sub-ultrasonic frequencies to said bone tissue in said living body, wherein said bone tissue includes said bone graft material; and
    (d) exposing said bone tissue to said mechanical stimulus at sub-ultrasonic frequencies in conjunction with said bone growth factor for a prescribed period of time,
    to produce a nonlinear interaction between said bone tissue, said mechanical stimulus at sub-ultrasonic frequencies and said bone growth factor, and
    to thereby synergistically promote bone tissue healing, growth, ingrowth and repair.

4. A method of therapeutically treating bone tissue in a living body, the method comprising the steps of:
    (a) applying a prescribed amount of a bone growth factor to an orthopaedic implant;
    (b) surgically implanting said orthopaedic implant including said bone growth factor within said bone tissue in said living body;
    (c) applying a mechanical stimulus at sub-ultrasonic frequencies to said bone tissue in said living body, wherein said bone tissue includes said orthopaedic implant; and
    (d) exposing said bone tissue to said mechanical stimulus at sub-ultrasonic frequencies in conjunction with said bone growth factor for a prescribed period of time,
    to produce a nonlinear interaction between said bone tissue, said mechanical stimulus at sub-ultrasonic frequencies and said bone growth factor, and
    to thereby synergistically promote bone tissue healing, growth, ingrowth and repair.

5. A method of therapeutically treating bone tissue in a living body, the method comprising the steps of:
    (a) applying a prescribed amount of a bone growth factor to a bone graft material;
    (b) surgically implanting said bone graft material including said bone growth factor within said bone tissue in said living body;
    (c) applying an electromagnetic stimulus to said bone tissue in said living body, wherein said bone tissue includes said bone graft material; and
    (d) exposing said bone tissue to said electromagnetic stimulus in conjunction with said bone growth factor for a prescribed period of time,
    to produce a nonlinear interaction between said bone tissue, said electromagnetic stimulus and said bone growth factor, and
    to thereby synergistically promote bone tissue healing, growth, ingrowth and repair.

6. A method of therapeutically treating bone tissue in a living body, the method comprising the steps of:
    (a) applying a prescribed amount of a bone growth factor to an orthopaedic implant;
    (b) surgically implanting said orthopaedic implant including said bone growth factor within said bone tissue in said living body;
    (c) applying an electromagnetic stimulus to said bone tissue in said living body, wherein said bone tissue includes said orthopaedic implant; and
    (d) exposing said bone tissue to said electromagnetic stimulus in conjunction with said bone growth factor for a prescribed period of time,
    to produce a nonlinear interaction between said bone tissue, said electromagnetic stimulus and said bone growth factor, and
    to thereby synergistically promote bone tissue healing, growth, ingrowth and repair.

7. A method of therapeutically treating bone tissue in a living body, the method comprising the steps of:
    (a) applying exogenously a prescribed amount of a bone growth factor to said living body;
    (b) applying an electromagnetic stimulus to said bone tissue in said living body; and
    (c) exposing said bone tissue to said electromagnetic stimulus in conjunction with said bone growth factor for a prescribed time period,
    to produce nonlinear interaction between said bone tissue, said electromagnetic stimulus, and said bone growth factor, said nonlinear interaction arising from a concurrent use of said electromagnetic stimulus and said bone growth factor during said prescribed time period, and
    to synergistically promote bone tissue healing, growth, and repair.

8. The method according to claim 7, wherein said nonlinear interaction includes diffusion of molecules of said bone growth factor by said electromagnetic stimulus.

9. The method according to claim 7, wherein said nonlinear interaction includes microstirring of molecules of said bone growth factor by said electromagnetic stimulus.

10. The method according to claim 7, wherein said nonlinear interaction includes binding of molecules of said bone growth factor to cells in said bone tissue.

11. The method according to claim 7, wherein said nonlinear interaction includes a change in a binding constant associated with said bone growth factor and cells in said bone tissue.

12. The method according to claim 7, wherein said nonlinear interaction includes an increase in temperature.

13. The method according to claim 7, wherein said nonlinear interaction includes an increase in local blood flow.

14. The method according to claim 7, wherein said bone growth factor is a bone morphogenic protein.

15. The method according to claim 7, wherein said bone growth factor is TGF-E.

16. The method according to claim 7, wherein said bone growth factor is a fibroblast growth factor.

17. The method according to claim 7, wherein said bone growth factor is a platelet-derived growth factor.

18. The method according to claim 7, wherein said bone growth factor is an osteogenic protein.

19. The method according to claim 7, wherein said bone growth factor is DNA.

20. The method according to claim 7, wherein said bone growth factor is RNA.

21. The method according to claim 7, wherein said applying an electromagnetic stimulus is performed inductively.

22. The method according to claim 7, wherein said applying an electromagnetic stimulus is through electrodes in contact with said living body.

23. The method according to claim 7, wherein said bone growth factor is contained in a biocompatible matrix.

24. A method of therapeutically treating bone tissue in a living body, the method comprising the steps of:
   (a) applying exogenously a prescribed amount of a bone growth factor to said living body;
   (b) applying a mechanical stimulus at sub-ultrasonic frequencies to said bone tissue in said living body; and
   (c) exposing said bone tissue to said mechanical stimulus at sub-ultrasonic frequencies in conjunction with said bone growth factor for a prescribed time period,
   to produce nonlinear interaction between said bone tissue, said mechanical stimulus at sub-ultrasonic frequencies, and said bone growth factor, said nonlinear interaction arising from a concurrent use of said mechanical stimulus at sub-ultrasonic frequencies and said bone growth factor during said prescribed time period, and
   to thereby synergistically promote bone tissue healing, growth, and repair.

25. The method according to claim 24, wherein said nonlinear interaction includes diffusion of molecules of said bone growth factor by said mechanical stimulus at sub-ultrasonic frequencies.

26. The method according to claim 24, wherein said nonlinear interaction includes microstirring of molecules of said bone growth factor by said mechanical stimulus at sub-ultrasonic frequencies.

27. The method according to claim 24, wherein said nonlinear interaction includes binding of molecules of said bone growth factor to cells in said bone tissue.

28. The method according to claim 24, wherein said nonlinear interaction includes a change in a binding constant associated with said bone growth factor and cells in said bone tissue.

29. The method according to claim 24, wherein said nonlinear interaction includes an increase in temperature.

30. The method according to claim 24, wherein said nonlinear interaction includes an increase in local blood flow.

31. The method according to claim 24, wherein said bone growth factor is a bone morphogenic protein.

32. The method according to claim 24, wherein said bone growth factor is TGF-E.

33. The method according to claim 24, wherein said bone growth factor is a fibroblast growth factor.

34. The method according to claim 24, wherein said bone growth factor is a platelet-derived growth factor.

35. The method according to claim 24, wherein said bone growth factor is an osteogenic protein.

36. The method according to claim 24, wherein said bone growth factor is DNA.

37. The method according to claim 24, wherein said bone growth factor is RNA.

38. The method according to claim 24, wherein said bone growth factor is contained in a biocompatible matrix.

39. The method according to claim 24, wherein said mechanical stimulus at sub-ultrasonic frequencies is dynamization.

40. The method according to claim 24, wherein said mechanical stimulus at sub-ultrasonic frequencies is a vibrating platform.

41. The method according to claim 24, wherein said mechanical stimulus at sub-ultrasonic frequencies is a vibration shaker.

42. A method of therapeutically treating cartilage tissue in a living body, the method comprising the steps of:
   (a) applying exogenously a prescribed amount of a biochemical compound to said living body;
   (b) applying an ultrasound stimulus to said cartilage tissue in said living body; and
   (c) exposing said cartilage tissue to said ultrasound stimulus in conjunction with said biochemical compound for a prescribed time period,
   to produce nonlinear interaction between said cartilage tissue, said ultrasound stimulus, and said biochemical compound, said nonlinear interaction arising from a concurrent use of said ultrasound stimulus and said biochemical compound during said prescribed time period, and
   to thereby synergistically promote cartilage tissue healing, growth, and repair.

43. The method according to claim 42, wherein said biochemical compound is sodium hyaluronate.

44. A method of therapeutically treating cartilage tissue in a living body, the method comprising the steps of:
   (a) applying exogenously a prescribed amount of a biochemical compound to said living body;
   (b) applying an electromagnetic stimulus to said cartilage tissue in said living body; and
   (c) exposing said cartilage tissue to said electromagnetic stimulus in conjunction with said biochemical compound for a prescribed time period,
   to produce nonlinear interaction between said cartilage tissue, said electromagnetic stimulus, and said biochemical compound, said nonlinear interaction arising from a concurrent use of said electromagnetic stimulus and said biochemical compound during said prescribed time period, and to thereby synergistically promote cartilage tissue healing, growth, and repair.

45. The method according to claim 44, wherein said biochemical compound is sodium hyaluronate.

46. A method of therapeutically treating cartilage tissue in a living body, the method comprising the steps of:
   (a) applying exogenously a prescribed amount of a biochemical compound to said living body;
   (b) applying a mechanical stimulus at sub-ultrasonic frequencies to said cartilage tissue in said living body; and
   (c) exposing said cartilage tissue to said mechanical stimulus at sub-ultrasonic frequencies in conjunction with said biochemical compound for a prescribed time period,
   to produce nonlinear interaction between said cartilage tissue, said mechanical stimulus at sub-ultrasonic frequencies, and said biochemical compound, said nonlinear interaction arising from a concurrent use of said mechanical stimulus at sub-ultrasonic frequencies and said biochemical compound during said prescribed time period, and
   to thereby synergistically promote cartilage tissue healing, growth, and repair.

47. The method of claim 46, wherein said biochemical compound is sodium hyaluronate.

48. A method of therapeutically treating ligament tissue in a living body, the method comprising the steps of:
   (a) applying exogenously a prescribed amount of a biochemical compound to said living body;
   (b) applying an ultrasound stimulus to said ligament tissue in said living body; and
   (c) exposing said ligament tissue to said ultrasound stimulus in conjunction with said biochemical compound for a prescribed time period,
   to produce nonlinear interaction between said ligament tissue, said ultrasound stimulus, and said biochemical compound, said nonlinear interaction arising from a concurrent use of said ultrasound stimulus and said biochemical compound during said prescribed time period, and
   to thereby synergistically promote ligament tissue healing, growth, and repair.

49. A method of therapeutically treating ligament tissue in a living body, the method comprising the steps of:
   (a) applying exogenously a prescribed amount of a biochemical compound to said living body;
   (b) applying an electromagnetic stimulus to said ligament tissue in said living body; and
   (c) exposing said ligament tissue to said electromagnetic stimulus in conjunction with said biochemical compound for a prescribed time period,
   to produce nonlinear interaction between said ligament tissue, said electromagnetic stimulus, and said biochemical compound, said nonlinear interaction arising from a concurrent use of said electromagnetic stimulus and said biochemical compound during said prescribed time period, and
   to thereby synergistically promote ligament tissue healing, growth, and repair.

50. A method of therapeutically treating ligament tissue in a living body, the method comprising the steps of:
   (a) applying exogenously a prescribed amount of a biochemical compound to said living body;
   (b) applying a mechanical stimulus at sub-ultrasonic frequencies to said ligament tissue in said living body; and
   (c) exposing said ligament tissue to said mechanical stimulus at sub-ultrasonic frequencies in conjunction with said biochemical compound for a prescribed time period,
   to produce nonlinear interaction between said ligament tissue, said mechanical stimulus at sub-ultrasonic frequencies, and said biochemical compound, said nonlinear interaction arising from a concurrent use of said mechanical stimulus at sub-ultrasonic frequencies and said biochemical compound during said prescribed time period, and
   to thereby synergistically promote ligament tissue healing, growth, and repair.

51. A method of therapeutically treating tendon tissue in a living body, the method comprising the steps of:
   (a) applying exogenously a prescribed amount of a biochemical compound to said living body;
   (b) applying an ultrasound stimulus to said tendon tissue in said living body; and
   (c) exposing said tendon tissue to said ultrasound stimulus in conjunction with said biochemical compound for a prescribed time period,
   to produce nonlinear interaction between said tendon tissue, said ultrasound stimulus, and said biochemical compound, said nonlinear interaction arising from a concurrent use of said ultrasound stimulus and said biochemical compound during said prescribed time period, and
   to thereby synergistically promote tendon tissue healing, growth, and repair.

52. A method of therapeutically treating tendon tissue in a living body, the method comprising the steps of:
   (a) applying exogenously a prescribed amount of a biochemical compound to said living body;
   (b) applying an electromagnetic stimulus to said tendon tissue in said living body; and
   (c) exposing said tendon tissue to said electromagnetic stimulus in conjunction with said biochemical compound for a prescribed time period,
   to produce nonlinear interaction between said tendon tissue, said electromagnetic stimulus, and said biochemical compound, said nonlinear interaction arising from a concurrent use of said electromagnetic stimulus and said biochemical compound during said prescribed time period, and
   to thereby synergistically promote tendon tissue healing, growth, and repair.

53. A method of therapeutically treating tendon tissue in a living body, the method comprising the steps of:
   (a) applying exogenously a prescribed amount of a biochemical compound to said living body;
   (b) applying a mechanical stimulus at sub-ultrasonic frequencies to said tendon tissue in said living body; and
   (c) exposing said tendon tissue to said mechanical stimulus at sub-ultrasonic frequencies in conjunction with said biochemical compound for a prescribed time period,
   to produce nonlinear interaction between said tendon tissue, said mechanical stimulus at sub-ultrasonic frequencies, and said biochemical compound, said nonlinear interaction arising from a concurrent use of said mechanical stimulus at sub-ultrasonic frequencies and said biochemical compound during said prescribed time period, and
to thereby synergistically promote tendon tissue healing, growth, and repair.

54. A method of non-invasively applying a bone growth factor to bone tissue in a living body, using an ultrasound transducer and an ultrasound pulser, the method comprising the steps of:
   (a) placing a prescribed amount of said bone growth factor on skin overlying said bone tissue in said living body;
   (b) acoustically coupling said ultrasound transducer to said skin overlying said bone tissue of said living body;
   (c) connecting said ultrasound pulser to said ultrasound pulser and thereby generating an ultrasound signal within said skin and said bone tissue; and
   (d) transporting said bone growth factor through said skin to said bone tissue using said ultrasound signal, wherein said bone tissue receives non-invasively said bone growth factor.

55. A method of non-invasively applying sodium hyaluronate to cartilage tissue in a living body, using an ultrasound transducer and an ultrasound pulser, the method comprising the steps of:
   (a) placing a prescribed amount of said sodium hyaluronate on skin overlying said cartilage tissue in said living body;
   (b) acoustically coupling said ultrasound transducer to said skin overlying said bone tissue of said living body;
   (c) connecting said ultrasound pulser to said ultrasound pulser and thereby generating an ultrasound signal within said skin and said cartilage tissue; and
   (d) transporting said sodium hyaluronate through said skin to said cartilage tissue using said ultrasound signal, wherein said bone tissue receives non-invasively said sodium hyaluronate.

56. A method of therapeutically treating musculoskeletal tissue in a living body, the method comprising the steps of:
   (a) applying exogenously a prescribed amount of a biochemical compound to said living body;
   (b) applying a biophysical stimulus to said musculoskeletal tissue in said living body; and
   (c) exposing said musculoskeletal tissue to said biophysical stimulus in conjunction with said biochemical compound for a prescribed time period,
   to produce nonlinear interaction between said musculoskeletal tissue, said biophysical stimulus, and said biochemical compound, said nonlinear interaction arising from a concurrent use of said biophysical stimulus and said biochemical compound during said prescribed time period, and
   to thereby synergistically promote musculoskeletal tissue healing, growth, and repair.

57. The method according to claim 56, wherein said musculoskeletal tissue includes bone tissue, said biochemical compound includes a bone growth factor, and said biophysical stimulus includes ultrasound.

58. The method according to claim 57, wherein said nonlinear interaction includes diffusion of molecules of said bone growth factor by said ultrasound stimulus.

59. The method according to claim 57, wherein said nonlinear interaction includes microstirring of molecules of said bone growth factor by said ultrasound stimulus.

60. The method according to claim 57, wherein said nonlinear interaction includes binding of molecules of said bone growth factor to cells in said bone tissue.

61. The method according to claim 57, wherein said nonlinear interaction includes a change in a binding constant associated with said bone growth factor and cells in said bone tissue.

62. The method according to claim 57, wherein said nonlinear interaction includes an increase in temperature.

63. The method according to claim 57, wherein said nonlinear interaction includes an increase in local blood flow.

64. The method according to claim 57, wherein said bone growth factor is a bone morphogenic protein.

65. The method according to claim 57, wherein said bone growth factor is TGF-$\beta$.

66. The method according to claim 57, wherein said bone growth factor is a fibroblast growth factor.

67. The method according to claim 57, wherein said bone growth factor is a platelet-derived growth factor.

68. The method according to claim 57, wherein said bone growth factor is an osteogenic protein.

69. The method according to claim 57, wherein said bone growth factor is DNA.

70. The method according to claim 57, wherein said bone growth factor is RNA.

71. The method according to claim 57, wherein said ultrasound stimulus is a broadband exponentially damped sinusoidal signal.

72. The method according to claim 57, wherein said ultrasound stimulus is a sine wave having a decreasing amplitude over time.

73. The method according to claim 57, wherein said ultrasound stimulus is a continuous sinusoidal signal.

74. The method according to claim 57, wherein said ultrasound stimulus is a pulsed sinusoidal signal.

75. The method according to claim 57, wherein said ultrasound stimulus is a broadband repetitive pulse.

76. The method according to claim 57, wherein said ultrasound stimulus is an amplitude-modulated waveform.

77. The method according to claim 57, wherein said ultrasound stimulus is a frequency-modulated waveform.

78. The method according to claim 56, wherein said bone growth factor is contained in a biocompatible matrix.

79. The method of claim 56, wherein said biophysical stimulus is an ultrasound stimulus.

80. The method of claim 56, wherein said biophysical stimulus is a mechanical stimulus at sub-ultrasonic frequencies.

81. The method of claim 56, wherein said biophysical stimulus is an electromagnetic stimulus.

82. The method of claim 56, wherein said musculoskeletal tissue is bone tissue.

83. The method of claim 56, wherein said musculoskeletal tissue is cartilage tissue.

84. The method of claim 56, wherein said musculoskeletal tissue is ligament tissue.

85. The method of claim 56, wherein said musculoskeletal tissue is tendon tissue.

86. The method of claim 56, wherein said biophysical stimulus is an ultrasound stimulus and wherein said musculoskeletal tissue is bone tissue.

87. The method of claim 86, wherein said bone tissue contains a surgically implanted bone graft material.

88. The method of claim 87, wherein said biochemical compound is a bone growth factor.

89. The method of claim 88, wherein said applying exogenously a prescribed amount of a bone growth factor to said living body includes applying said prescribed amount of said bone growth factor to said bone graft material.

90. The method of claim 86, wherein said bone tissue contains a surgically implanted orthopaedic implant.

91. The method of claim 90, wherein said biochemical compound is a bone growth factor.

92. The method of claim 91, wherein said applying exogenously a prescribed amount of a bone growth factor to said living body includes applying said prescribed amount of said bone growth factor to said orthopaedic implant.

* * * * *

UNITED STATES PATENT AND TRADEMARK OFFICE
CERTIFICATE OF CORRECTION

PATENT NO.    : 6,652,473 B2
DATED         : November 25, 2003
INVENTOR(S)   : Jonathan J. Kaufman et al.

It is certified that error appears in the above-identified patent and that said Letters Patent is hereby corrected as shown below:

Signed and Sealed this

Twenty-seventh Day of April, 2004

JON W. DUDAS
*Acting Director of the United States Patent and Trademark Office*

UNITED STATES PATENT AND TRADEMARK OFFICE
CERTIFICATE OF CORRECTION

PATENT NO. : 6,652,473 B2
DATED : November 25, 2003
INVENTOR(S) : Jonathan J. Kaufman et al.

It is certified that error appears in the above-identified patent and that said Letters Patent is hereby corrected as shown below:

Column 24,
Line 42, the claim reference numeral "56", should read -- 57 --.

Signed and Sealed this

Twenty-seventh Day of April, 2004

JON W. DUDAS
*Acting Director of the United States Patent and Trademark Office*

UNITED STATES PATENT AND TRADEMARK OFFICE
CERTIFICATE OF CORRECTION

PATENT NO. : 6,652,473 B2
DATED : November 25, 2003
INVENTOR(S) : Jonathan J. Kaufman et al.

It is certified that error appears in the above-identified patent and that said Letters Patent is hereby corrected as shown below:

Column 24,
Line 42, the claim reference numeral "56", should read -- 57 --.

This certificate supersedes Certificate of Correction issued April 27, 2004.

Signed and Sealed this

Thirty-first Day of August, 2004

JON W. DUDAS
*Acting Director of the United States Patent and Trademark Office*